United States Patent [19]

George et al.

[11] Patent Number: 5,683,873

[45] Date of Patent: Nov. 4, 1997

[54] EGS-MEDIATED INACTIVATION OF TARGET RNA

[75] Inventors: Shaji T. George, New York; Michael Ma, Roosevelt Island; Martina Werner, New York; Umberto Pace, Riverdale; Allan R. Goldberg, New York, all of N.Y.

[73] Assignee: Innovir Laboratories, Inc., New York, N.Y.

[21] Appl. No.: 372,556

[22] Filed: Jan. 13, 1995

[51] Int. Cl.⁶ .................... C12Q 1/68; A61K 48/00; C07H 21/02; C07H 21/04
[52] U.S. Cl. .................... 435/6; 514/44; 536/23.1; 536/24.5; 435/320.1
[58] Field of Search .................... 424/94.3, 450, 424/172.1, 199; 435/69.1, 91.31, 91.4, 199, 172.1, 320.1, 6; 514/44; 536/23.2, 25.1, 25.2, 24.5

[56] References Cited

U.S. PATENT DOCUMENTS

| | | | |
|---|---|---|---|
| 4,868,116 | 9/1989 | Morgan et al. | 435/240.2 |
| 4,980,286 | 12/1990 | Morgan et al. | 435/172.3 |
| 5,168,053 | 12/1992 | Altman et al. | 514/44 |
| 5,225,347 | 7/1993 | Goldberg et al. | 435/320.1 |
| 5,334,711 | 8/1994 | Sproat et al. | 536/24.5 |
| 5,525,719 | 6/1996 | Srivastava et al. | 536/26.7 |

FOREIGN PATENT DOCUMENTS

| | | | |
|---|---|---|---|
| 0 321 021 | 6/1989 | European Pat. Off. | H04L 7/02 |
| WO 88/04300 | 6/1988 | WIPO | C07H 17/02 |
| WO 89/05852 | 6/1989 | WIPO | C12N 9/22 |
| WO 89/07136 | 8/1989 | WIPO | C12N 5/00 |
| WO 90/02176 | 3/1990 | WIPO | C12N 15/00 |
| WO 90/02806 | 3/1990 | WIPO | C12N 15/86 |
| WO 91/04319 | 4/1991 | WIPO | C12N 7/01 |
| WO 91/04324 | 4/1991 | WIPO | C12N 9/22 |
| WO 1/16420 | 10/1991 | WIPO | C12N 7/06 |
| WO 92/03566 | 3/1992 | WIPO | C12P 19/34 |
| WO 93/01286 | 1/1993 | WIPO | C12N 15/11 |
| WO 93/22434 | 11/1993 | WIPO | |
| WO 94/13791 | 6/1994 | WIPO | |
| WO 95/24489 | 9/1995 | WIPO | |
| WO 96/18733 | 6/1996 | WIPO | |

OTHER PUBLICATIONS

Milligan et. al. J. of Medicinal Chemistry, Jul. 9, 1993, vol. 36 (14): 1923–1936.
Christoffersen and Marr, J. of Medicinal Chemistry, Jun. 9, 1995, vol 38 (12): 2023–2037.
Gaur, et al., Nucl. Acids Res. 21(1), 21–26 (Jan. 11, 1993).
Ma, et al., J. Cell. Biochem. Supp. 211, 5–26, (Jan. 1995).
Symons, Curr. Op. Struct. Biol. 4(3), 322–330 (Jun. 1, 1994).
Usman, et al., Nuc. Acids. Res. Symp. Ser. 31, 163–164 (Nov. 9, 1994)).
Agrawal et al., "Oligodeoxynucleoside phosphoramidates and phosphorothioates as inhibitors of human immunodeficiency virus," Proc. Natl. Acad. Sci. USA, 85:7079–7083 (1988).
Altman, S., "RNA enzyme–directed gene therapy," Proc. Natl. Acad. Sci. USA 90:10898–10900 (1993).

(List continued on next page.)

Primary Examiner—David Guzo
Assistant Examiner—William Sandals
Attorney, Agent, or Firm—Arnall Golden & Gregory, LLP

[57] ABSTRACT

Modified external guide sequence (EGS) molecules that mediate cleavage of specific target RNAs have been constructed. The modified molecules are external guide sequence molecules for RNAse P which are designed to specifically bind to and promote RNAse P-mediated cleavage of target RNA molecules and to have enhanced nuclease resistance. Specific regions are modified to achieve enhanced stability while maintaining RNAse P activity. Modified external guide sequence molecules suitable for use in the treatment of hepatitis B viral infections have been constructed.

29 Claims, 8 Drawing Sheets

OTHER PUBLICATIONS

Bartkiewicz et al., "Identification and characterization of an RNA molecule that copurifies with RNase P activity from HeLa cells," *Genes Dev.* 3:488–499 (1989).

Cech, T., "Self–Splicing Of Group I Introns," *Annu. Rev. Biochem.*, 59:543–568, (1990).

Clarenc, J.P., et al., "Delivery of antisense oligonucleotides by poly(L–lysine) conjugation and liposome encapsulation," *Anti–Cancer Drug Design,* 8:81–94 (1993).

Felgner, P.L. et al., "Lipofection: A highly efficient, lipid-–mediated DNA–transfection procedure," *Proc. Natl. Acad. Sci. USA,* 84:7413–7417 (1987).

Felgner, P.L., "Particulate systems and polymers for in vitro and in vivo delivery of polynucleotides," *Advanced Drug Delivery Reviews,* 5:163–187 (1990).

Felgner, P.L. et al., "Cationic liposome–mediated transfection," *Nature,* 337:387–388 (1989).

Forster, A.C. and Altman, "External Guide Sequences for an RNA Enzyme," S., *Science,* 249:783–786 (1990).

Grigoriev et al., "A Triple Helix–forming Oligonucleotide–Intercalator Conjugate Acts as a Transcriptional Repressor via Inhibition of NF kB Binding to Interleukin–2 Receptor α–Regulatory Sequence," *J. Biol. Chem.,* 267:3389–3395 (1992).

Guerrier–Takada, C., et al., "The RNA Moiety of Ribonuclease P Is the Catalytic Subunit of the Enzyme," *Cell,* 35:849–857 (1983).

Heidenreich and Eckstein, "Hammerhead Ribozyme–mediated Cleavage of the Long Terminal Repeat RNA of Human Immunodeficiency Virus Type 1," *J. Biol. Chem.,* 267:1904–1909 (1992).

Hoke et al., "Effects of phosphorothioate capping on antisense oligonucleotide stability, hybridization and antiviral efficacy versus herpes simplex virus infection," *Nucleic Acids Res.* 19:5743–5748 (1991).

Ikuta et al., "Synthesis and use of Synthetic Oligonucleotides," *Ann. Rev. Biochem.,* 53:323–356 (1984).

P. Johnson and J.G. Lloyd–Jones. eds., *Drug Delivery Systems* (Chichester, England: Ellis Horwood Ltd., 1987).

Kim, et al., "Preparation of Multivesicular liposomes," *Biochim. Biophys. Acta.* 728:339–348 (1983).

Lee, et al., "Recognition of liposomes by cells: in vitro binding and endocytosis mediated by specific lipid headgroups and surface charge density," *Biochim. Biophys. Acta.,* 1103:185–197 (1992).

Liu, D., et al., "Role of liposome size and RES blockade in controlling biodistribution and tumor uptake of $GM_1$–containing liposomes," *Biochim. Biophys. Acta,* 1104:95–101 (1992).

Maher et al., "Inhibition of DNA Binding Proteins by Oligonucleotide–Directed Triple Helix Formation," *Science,* 245:725–730 (1989).

Milligan, et al., "Oligoribonucleotide synthesis using T7 RNA polymerase and synthetic DNA templates" *Nucl Acids Res.,* 15:8783 (1987).

Mulligan, "The Basic Science of Gene Therapy," *Science,* 260:926–932 (1993).

Narang et al., "Chemical Synthesis of Deoxyoligonucleotides by the Modified Triester Method," *Methods Enzymol.,* 65:610–620 (1980).

Offensperger et al., "In vivo inhibition of duck hepatitis B virus replication and gene expression by phosphorothioate modified antisense oligodeoxynucleotides" *EMBO J.,* 12:1257–1262 (1993).

Ogilvie et al., "Total chemical synthesis of a 77–nucleotide–long RNA sequence having methionine–acceptance activity," *Proc. Natl. Acad. Sci. U.S.A.,* 85:5764–5768 (1988).

Orson et al., "Oligonucleotide inhibition of IL2Rα mRNA transcription by promoter region collinear triplex formation in lymphocytes," *Nucl. Acids Res.,* 19:3435–3441 (1991).

Paolella et al., "Nuclease resistant ribozymes with high catalytic activity" *EMBO J.,* 11:1913–1919 (1992).

Pieken, et al., "Kinetic Characterization of Ribonuclease–Resistant 2'–Modified Hammerhead Ribozymes," *Science,* 253:314–317 (1991).

Pugh, 1990*.

Robinson, 1990*.

Rossi, J.J., et al., "Exploring the Use of Antisense, Enzymatic RNA Molecules (Ribozymes) as Therapeutic Agents" *Antisense Res. Dev.,* 1:285–288 (1991).

Sarin et al., "Inhibition of acquired immunodeficiency syndrome virus by oligodeoxynucleoside methylphosphonates," *Proc. Natl. Acad. Sci, USA,* 85:7448–7794 (1989).

Scaringe et al., "Chemical synthesis of biologically active oligoribonucleotides using β–cyanoethyl protected ribonucleoside phosphoramidites," *Nucleic Acids Research,* 18:5433–5441 (1990).

Seela, F. and Kaiser, K., "Oligodeoxyribonucleotides containing 1,3–propanediol as nucleoside substitute," *Nucleic Acids Res.,* 15:3113–3129 (1987).

Shaw et al., "Modified deoxyoligonucleotides stable to exonuclease degradation in serum," *Nucleic Acids Res.* 19:747–750 (1991).

Symons R.H., "Small Catalytic RNAs," *Annu. Rev. Biochem.,* 61:641–671 (1992).

Thierry, A.R. and Dritschilo, A., "Intracellular availability of unmodified, phosphorothioated and liposomally encapsulated oligodeoxynucleotides for antisense activity," *Nucl. Acids Res.,* 20:5691–5698 (1992).

Wang, et al., "Highly Efficient DNA Delivery Mediated by pH–Sensitive Immunoliposomes," *Biochem.,* 28:9508–9514 (1989).

Yuan, Y. and Altman, S., "Selection of Guide Sequences That Direct Efficient Cleavage of mRNA by Human Ribonuclease P," *Science,* 263:1269–1273 (1994).

Yuan. Y., Hwayng, E.S. and Altman, S., "Targeted cleavage of mRNA by human RNase P," *Proc. Natl. Acad. Sci., USA,* 89:8006–8010 (1992).

Zhu et al., "Systemic Gene Expression After Intravenous DNA Delivery into Adult Mice," *Science,* 261:209–211 (1993).

S: 2'-OMe RNA(PS)
X & ACGU: 2'-OMe RNA(PO)
ACGU: RNA (PS)

INNO-102

INNO-108

INNO-109

INNO-110

INNO-111

INNO-139

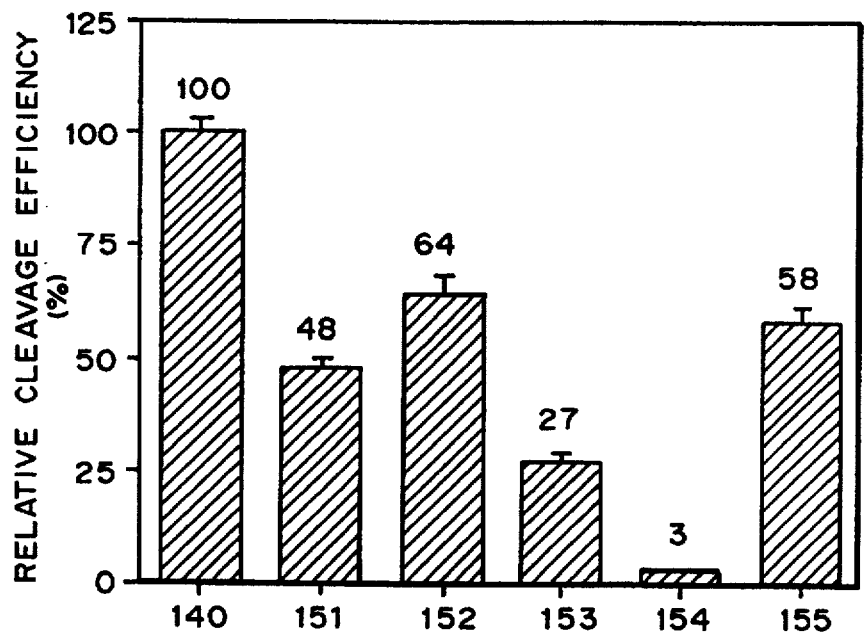
FIG. 6
FIG. 7
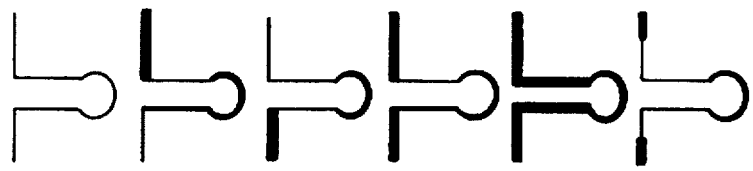
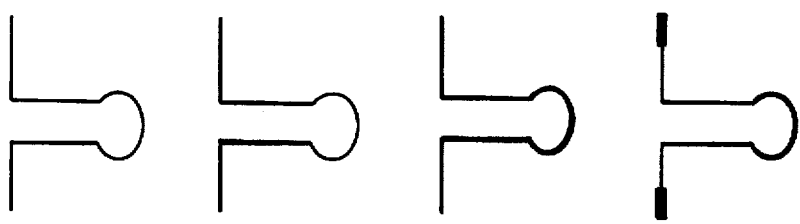
— RNA(PO)
— RNA(PS)
— 2'-OMe RNA(PO)
— 2'-OMe RNA(PS)

X = OH, -OPO(O)OCH$_2$CH(OH)CH$_2$NH$_2$,
-OPO(S)OCH$_2$CH(OH)CH$_2$NH$_2$
*ACGU* = 2'-OMe RNA (PS)
ACGU = 2'-OMe RNA (PO)
AUCG = RNA (PS)

X = OH, -OPO(O)OCH$_2$CH(OH)CH$_2$NH$_2$,
-OPO(S)OCH$_2$CH(OH)CH$_2$NH$_2$
*ACGU* = 2'-OMe RNA (PS)
ACGU = 2'-OMe RNA (PO)
AUCG = RNA (PS)

X = OH, -OPO(O)OCH$_2$CH(OH)CH$_2$NH$_2$,
    -OPO(S)OCH$_2$CH(OH)CH$_2$NH$_2$

N' = 2'-OMe RNA(PS) or 2'-OMe RNA
     (PO) or combinations of both

ACGU = 2'-OMe RNA(PO)

ACGU = RNA(PS)

X = OH, -OPO(O)OCH$_2$CH(OH)CH$_2$NH$_2$,
    -OPO(S)OCH$_2$CH(OH)CH$_2$NH$_2$

N' = 2'-OMe RNA(PS) or 2'-OMe RNA
     (PO) or combinations of both

N = 2'-OMe RNA(PO)

D = RNA(PS) OR RNA(PO)

M = RNA(PS) or 2'-OMe RNA(PO)

EGS-MEDIATED INACTIVATION OF TARGET RNA

BACKGROUND OF THE INVENTION

This application is directed to methods and external guide sequence compositions designed to target cleavage of RNA by RNAse P.

I. Ribozymes and External Guide Sequence Molecules

Ribonucleic acid (RNA) molecules can serve not only as carriers of genetic information, for example, genomic retroviral RNA and messenger RNA (mRNA) molecules and as structures essential for protein synthesis, for example, transfer RNA (tRNA) and ribosomal RNA (rRNA) molecules, but also as enzymes which specifically cleave nucleic acid molecules. Such catalytic RNA molecules are called ribozymes.

The discovery of catalytic RNA, by Drs. Altman and Cech, who were awarded the Nobel prize in 1989, has generated much interest in commercial applications, particularly in therapeutics (Altman, S., *Proc. Natl. Acad. Sci. USA* 90, 10898–10900 (1993); Symons R. H., *Annu. Rev. Biochem.*, 61, 641–671 (1992); Rossi, J. J., et al., *Antisense Res. Dev.*, 1, 285–288 (1991); Cech, T., *Annu. Rev. Biochem.*, 59, 543–568, (1990)). Several classes of catalytic RNAs (ribozymes) have been described, including intron-derived ribozymes (PCT/US87/03161, published as WO 88/04300 16 Jun. 1988, see also, Cech, T., *Annu. Rev. Biochem.*, 59, 543–568, (1990)), hammerhead ribozymes (WO 89/05852 and EP 321021 by GeneShears), axehead ribozymes (WO 91/04319 and WO 91/04324 by Innovir).

B. RNAse P

A second class of ribozymes include the RNA portion of an enzyme, RNAse P, which is involved in the processing of transfer RNA (tRNA), a common cellular component of the protein synthesis machinery. Bacterial RNAse P includes two components, a protein (C5) and an RNA (M1). Sidney Altman and his coworkers demonstrated that the M1 RNA is capable of functioning just like the complete enzyme, showing that in *Escherichia coli* the RNA is essentially the catalytic component, (Guerrier-Takada, C., et al., *Cell*, 35, 849–857, (1983)). In subsequent work, Dr. Altman and colleagues developed a method for converting virtually any RNA sequence into a substrate for bacterial RNAse P by using an external guide sequence (EGS), having at its 5' terminus at least seven nucleotides complementary to the nucleotides 3' to the cleavage site in the RNA to be cleaved and at its 5' terminus the nucleotides NCCA (N is any nucleotide)(WO 92/03566 and Forster, A. C. and Altman, S., *Science*, 238, 407–409 (1990)). Using similar principles, EGS/RNAse P-directed cleavage of RNA has been developed for use in eukaryotic systems, (Yuan, Y., Hwang, E. S., and Altman, S., *Proc. Natl. Acad. Sci. USA*, 89, 8006–8010 (1992)). As used herein, "external guide sequence" and "EGS" refer to any oligonucleotide that forms an active cleavage site for RNAse P in a target RNA.

II. Hepatitis B Virus (HBV)

HBV, a member of a group of small DNA-containing viruses that cause persistent noncytopathic infections of the liver, is an infectious agent of humans that is found worldwide and which is perpetuated among humans in a large reservoir of chronic carriers. It is estimated that about 6–7% of the earth's population is infected (300 million carriers). The prevalence of the infection is not uniform throughout the world. There is a geographic gradient in distribution of HBV. It is lowest in North America and Western Europe, where the virus can be detected in 0.1 to 0.5% of the population, and highest in Southeast Asia and sub-Saharan Africa, where the frequency of infection may vary from 5 to 20% of the population. This skewed distribution parallels that of hepatocellular carcinoma and provides strong epidemiologic evidence for an association between chronic HBV infection and this type of malignancy.

Hepatitis B is of great medical importance because it is probably the most common cause of chronic liver disease, including hepatocellular carcinoma in humans. Infected hepatocytes continually secrete viral particles that accumulate to high levels in the blood. These particles are of two types: (i) noninfectious particles consisting of excess viral coat protein (HBsAg) and containing no nucleic acid (in concentrations of up to $10^{13}$ particles/ml blood), and (ii) infectious, DNA-containing particles (Dane particles) consisting of a 27 nm nucleocapsid core (HBcAg) around which is assembled an envelope containing the major viral coat protein, carbohydrate, and lipid, present in lower concentrations ($10^9$ particles/ml blood). The human hepatitis B virus is a member of the Hepadna Viridae family, with close relatives including woodchuck hepatitis virus (WHV), duck hepatitis virus (DHV), and ground squirrel hepatitis virus (GHV) (Robinson, 1990). Like retroviruses, the hepadnavirus utilizes reverse transcription of its 3.2 Kb DNA genome (Pugh, 1990). The genome of hepatitis B virus is circular and partially single-stranded, containing an incomplete plus strand. The incomplete plus strand is complexed with a DNA polymerase in the virion which has been shown to elongate the plus strand using the complete minus strand as the template. These morphological and structural features distinguish hepatitis B viruses from all known classes of DNA-containing viruses.

The replication cycle of hepatitis B viruses is also strikingly different from other DNA-containing viruses and suggests a close relationship with the RNA-containing retroviruses. The principal unusual feature is the use of an RNA copy of the genome as an intermediate in the replication of the DNA genome. Infecting DNA genomes are converted to a double-stranded form which serves as a template for transcription of RNA. Multiple RNA transcripts are synthesized from each infecting genome, which either have messenger function or DNA replicative function. The latter, termed "pre-genomes," are precursors of the progeny DNA genomes because they are assembled into nucleocapsid cores and reverse-transcribed into DNA before coating and export from the cell. Thus each mature virion contains a DNA copy of the RNA pre-genome and a DNA polymerase.

The first DNA to be synthesized is of minus strand polarity and is initiated at a unique site on the vital genetic map. Very small nascent DNA minus strands (less than 30 nucleotides) are covalently linked to a protein, and are likely to act as primer for minus strand DNA synthesis. Growth of the minus strand DNA is accompanied by a coordinate degradation of the pre-genome so that the product is a full-length single-stranded DNA, rather than an RNA:DNA hybrid. Plus strand DNA synthesis has been observed only after completion of the minus strand, and initiates at a unique site close to the 5' end of the minus strand. Complete elongation of the plus strand is not a requirement for coating and export of the nucleocapsid cores, thus most extracellular virions contain incomplete plus strands and a large single-stranded gap in their genomes. Because the hepatitis virus genome is autonomous and does not utilize a DNA-to-DNA pathway for its replication, continuous intracellular replication of its genome is essential for the maintenance of the virus.

The hepatitis B virus surface antigens (HBsAgs), which make up the viral envelope, are polypeptides encoded by the pre-S1, pre-S2 and S genes of the virus. The major protein is the 226 amino acid S gene product derived from a 2.1 kb subgenomic message.

It is therefore an object of the present invention to provide a therapeutic targeted for treatment of viral diseases, and method of use thereof.

It is another object of the present invention to provide modified external guide sequences for RNAse P with enhanced resistance to nuclease degradation.

It is another object of the present invention to provide methods of cleaving target RNA molecules mediated by modified external guide sequences for RNAse P.

It is a further object of the present invention to provide an external guide sequence for RNAse P specifically targeted against hepatitis, vectors encoding such external guide sequences, and methods of use thereof.

SUMMARY OF THE INVENTION

External guide sequence (EGS) molecules for eukayotic RNAse P are engineered to target efficient and specific cleavage of target RNA. Engineered RNA molecules are designed and synthesized which contain specific nucleotide sequences which enable an external guide sequence for RNAse P to preferentially bind to and promote RNAse P-mediated cleavage of hepatitis viral RNA. Modified versions of these engineered RNA molecules having modified nucleotides or nucleotide linkages are designed to enhance their resistance to nuclease degradation. Specific regions are modified to achieve enhanced stability while maintaining RNAse P targeting activity. Examples demonstrate that EGS molecules for RNAse P have been constructed that bind to and promote RNAse P cleavage of hepatitis viral RNA. Methods for the determination of the activity of an EGS, for the purpose of construct-screening, as well as methods for using and producing such RNA molecules, are also disclosed.

BRIEF DESCRIPTION OF THE DRAWINGS

FIG. 6 is a graph of the relative RNAse P cleavage efficiency (%) of various EGS molecules having the nucleotide sequence SEQ ID NO. 3. Modifications to each EGS are indicated diagrammatically underneath the corresponding graph bar. Unmodified regions are indicated by the thinnest line in the diagrams. Regions with only 2'-O-methyl modifications are indicated by the next thickest line in the diagrams. Regions with only 5'-phosphorothioate groups are indicated by the next thickest line in the diagrams. Regions with both 2'-O-methyl modifications and 5'-phosphorothioate groups are indicated by the thickest line in the diagrams.

FIG. 7 is a table showing the stability of modified EGS molecules in a Fetal Calf Serum Assay. For each EGS, relative cleavage activity (%) and half-life in the assay are shown. Modifications to each EGS are indicated diagrammatically underneath the corresponding table entry. Unmodified regions are indicated by the thinnest line in the diagrams. Regions with only 2'-O-methyl modifications are indicated by the next thickest line in the diagrams. Regions with only 5'-phosphorothioate groups are indicated by the next thickest line in the diagrams. Regions with both 2'-O-methyl modifications and 5'-phosphorothioate groups are indicated by the thickest line in the diagrams.

DETAILED DESCRIPTION OF THE INVENTION

Figure 2:
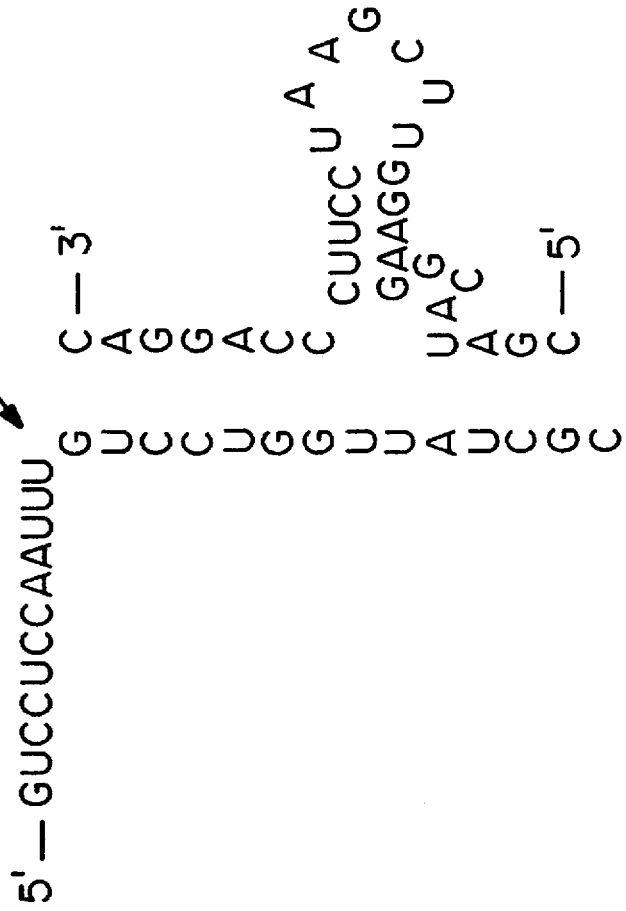
FIG. 2 is a diagram of the structure of an EGS with the nucleotide sequence SEQ ID NO. 2 and a short model target RNA with the nucleotide sequence SEQ ID NO. 1. The two oligonucleotides are aligned to show the base pairing which forms an RNAse P-like structure. The RNAse P cleavage site is indicated with an arrow.

RNA molecules suitable for promoting cleavage of target RNA molecules have been constructed. The RNA molecules are external guide sequence (EGS) molecules for RNAse P which are designed to specifically bind to and promote RNAse P-mediated cleavage of target RNA molecules and to have enhanced nuclease resistance. RNA molecules suitable for use in the treatment of hepatitis B viral infections have been constructed.

I. Design and Synthesis of EGS Molecules.

EGS molecules are synthetic oligonucleotides that bind to a target substrate to form a secondary and tertiary structure resembling the natural cleavage site of precursor tRNA for eukaryotic RNAse P. The ability of EGS molecules to target RNAse P activity is readily determined using an in vitro activity assay for cleavage by RNAse P of hepatitis RNA sequence, as described in more detail below. In the case of EGS molecules with modified nucleotides or nucleotide linkages, a stability assay allows determination of the nuclease resistance of various types of modification. The activity assay permits comparison of the efficiency of RNAse P cleavage mediated by EGS molecules with different modifications. Together, the assays are used to optimize and balance stability and cleavage efficiency of modified EGS molecules.

Example EGS molecules have been constructed which are suitable for use in the treatment of viral disease and cancer. The specific targets were the hepatitis B virus, more particularly, the hepatitis B surface antigen (HBsAg) encoding RNA. Since HBsAg plays an essential role in viral suprastructure and infection, EGS-based therapeutics can be used to down-regulate hepatitis through cleavage of HBsAg mRNA. Preferred targeted sites within hepatitis B RNA, or other target RNAs, are regions of conserved sequence which appear in all forms of the target RNA. Two such preferred sites have been identified in the HBsAg encoding region of hepatitis B RNA and are targeted by EGS molecules having nucleotide base sequences shown in SEQ ID NO. 5 and SEQ ID NO. 6.

Methods to produce or synthesize EGS molecules, and DNA sequences encoding EGS molecules having a known sequence, are now routine using automated nucleic acid synthesis, for example, using the cyanoethyl phosphoramidite method on a DNA model 392 synthesizer by Applied Biosystems, Inc. (Foster City, Calif.) or a Pharmacia Oligo Pilot (Pharmacia, Piscataway, N.J.). Other methods for synthesizing nucleic acid molecules are also available (see, for example, Ikuta et al., in *Ann. Rev. Biochem.*, 53: 323–356 (1984) (phosphotriester and phosphite-triester methods); Narang et al., in *Methods Enzymol.*, 65: 610–620 (1980) (phosphotriester method). Alternatively, EGS molecules can be synthesized by transcribing DNA templates, for example, with T7 RNA polymerase (Milligan, et al., *Nucl Acids Res.*, 15:8783 (1987)).

A. Activity of EGS Molecules

An in vitro cleavage assay which measures the percentage of substrate RNA remaining after incubation with various amounts of an engineered EGS, in the presence of a non-limiting amount of RNAse P, is used as an indicator of the potential activity of the EGS/RNAse P complex. EGS/RNAse P complexes that exhibit the highest in vitro activity are selected for further testing. The percentage of RNA remaining can be plotted as a function of the EGS concentration. The catalytic efficiency of an EGS/RNAse P can be expressed as $k_{cat}/K_m$ (where $k_{cat}$ is the rate constant of cleavage and $K_m$ is the Michaelis constant), the second order rate constant for the reaction of a free EGS and substrate RNA molecule. Following the methods of Heidenreich and Eckstein (*J. Biol. Chem.*, 267: 1904–1909 (1992)), $k_{cat}/K_m$ is determined using the formula $$-\ln F/t = (k_{cat}/K_m)[C]$$

where F is the fraction of substrate left, t is the reaction time, and [C] is the EGS concentration.

Preferred EGS constructs are those which bind to and promote the preferential RNAse P cleavage of the hepatitis substrate RNA. Preferred constructs can be selected using the ribozyme cleavage assay, as described in Example 1, and determining which constructs are the most efficient at mediating specific RNAse P cleavage of hepatitis substrate RNA sequence as determined by the value of $k_{cat}/K_m$, as described above.

B. Construction of EGS Molecules

EGS molecules can be designed by adapting the basic structure of a pre-tRNA molecule (pre-tRNA$^{Tyr}$) and adding substrate recognition sequences, as described, for example, in WO 92/03566, which is hereby incorporated by reference. For example, sequences complementary to the target sequences can be substituted for the sequences of the aminoacyl acceptor stem and the D stem. Such substituted sequences are referred to as recognition arms. The recognition arm corresponding to the aminoacyl acceptor stem is referred to as the A recognition arm and the recognition arm corresponding to the D stem is referred to as the D recognition arm. The remaining sequences, which correspond to tRNA sequence and structural elements, are referred to as cleavage targeting sequences. The sequence of the recognition arms are chosen to have regions specifically complementary to sequences in the target RNA immediately 3' of the desired cleavage site. The sequences of the recognition arms are chosen such that the complementary regions of the targeted sequence are adjacent to each other but separated by a small unpaired region. An example of this relationship is shown in FIG. 2. The recognition arms can be any length that results in a functional EGS molecule. In general, the 3'-terminal recognition arm should be at least seven nucleotides long and have a region complementary to the target RNA molecule at least seven nucleotides long.

Figure 1:
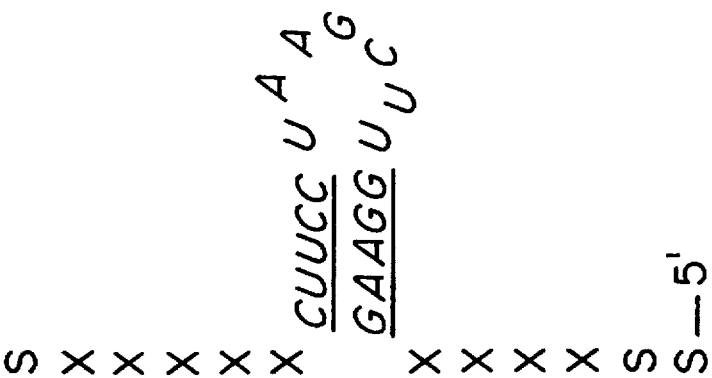
FIG. 1 is a diagram of the structure of an EGS with the nucleotide sequence SEQ ID NO. 4 and with chemical modifications in specific regions.

It has been discovered that, in addition to the recognition arms, functional EGS molecules require only a structure corresponding to the T stem and loop of precursor tRNA. Thus, a functional EGS molecule requires only a T stem and loop as its cleavage targeting sequence. The T stem and loop of an EGS molecule can be any length or sequence that results in a functional EGS molecule, that is, an EGS molecule that mediates RNAse P cleavage of a target RNA molecule. For example, any tRNA T loop sequence can be used. EGS molecules with loop lengths of 6, 7 and 8 nucleotides are functional. EGS molecules with limited sequence changes in the T loop, beyond the variations found in tRNA T loop sequences, also retain EGS function. The T stem can have any sequence which forms a stem structure. EGS molecules with stem lengths of 4, 5 and 6 base pairs are expected to be functional. A preferred T stem and loop sequence (nt 7 to 23 of SEQ ID NO. 4) is shown in FIG. 1. It has also been discovered that the extra, or variable, loop, which appears between the D stem and T stem in tRNA molecules, is not required for EGS function.

Accordingly, the EGS molecules described herein require only two recognition arms, complementary to a target sequence, attached to the 5' and 3' ends of a T stem and loop. EGS molecules may also contain additional sequences and structures corresponding to those found in tRNA precursor molecules, such as a D loop or a 3'-terminal NCCA sequence. Such additional sequences and structures are considered to be part of the cleavage targeting sequence. EGS molecules may also contain sequences at either or both distal ends that are not complementary to targeted sequences and are not related to tRNA structure. Such sequences are not considered to be a part of either the recognition sequence or the cleavage targeting sequence.

EGS molecules can be readily screened for the ability to promote cleavage, by RNAseP, of target RNA using the assay described in Yuan, Y., Hwayng, E. S. and Altman, S., *Proc. Natl. Acad. Sci., USA,* 89, 8006–8010, (1992).

The EGS molecules can also be regulatable. A regulatable EGS molecule is an EGS sequence, as described above, linked to a ligand-binding sequence, placing the activity of the EGS molecule under the control of that ligand and requiring the presence of the ligand for activation or inactivation. RNA molecules are constructed in which one portion is capable of binding a ligand and the other portion is an EGS sequence. After the selection of molecules which bind the ligand, a second selection process occurs in which the ligand-binding molecules are assayed for their catalytic function in the presence and absence of the ligand or "co-drug." In this manner regulatable EGS molecules are selected for use in cleaving a target RNA in the presence of a ligand, or in cleaving a target RNA in the absence of a ligand.

This method and regulatable EGS molecules are useful in cleaving a target RNA molecule in a controlled fashion. It is particularly useful when the target RNA molecule is present in a cell where it is not desirable to kill the host cell by complete inactivation of these RNA molecules. The formation, selection and use of regulatable EGS molecules is fully described in copending application U.S. Ser. No. 08/307,401 and copending application U.S. Ser. No. 08/240, 081, now U.S. Pat. No. 5,589,332 which are hereby incorporated by reference.

II. Nuclease Resistant EGS molecules.

A. Types of Modifications.

Although unmodified oligoribonucleotides can function as effective EGS in a nuclease-free environment, the short half-life in serum and inside cells reduces their effectiveness as therapeutics. Chemical modifications can be made which greatly enhance the nuclease resistance of EGS without compromising its biological function of inducing RNase P-mediated cleavage of RNA target. For example, one or more of the bases of an EGS construct can be replaced by 2' methoxy ribonucleotides or phosphorothioate deoxyribonucleotides using available nucleic acid synthesis methods (see, for example, Offensperger et. al., *EMBO J.*, 12: 1257–1262 (1993); PCT WO 93/01286 BY Rosenberg et al., (synthesis of sulfurthioate oligonucleotides); Agrawal et al., *Proc. Natl. Acad. Sci. USA*, 85: 7079–7083 (1988); Sarin et al., *Proc. Natl. Acad. Sci. USA*, 85: 7448–7794 (1989); Shaw et al., *Nucleic Acids Res*, 19: 747–750 (1991) (synthesis of 3' exonuclease-resistant oligonucleotides containing 3' terminal phosphoroamidate modifications); incorporated herein by reference).

It is well documented in the current literature that degradation of oligonucleotide analogues is mainly attributable to 3'-exonucleases. Several studies have also demonstrated that various 3'-modifications can greatly decrease the nuclease susceptibility of these analogues. Thus, another method to reduce susceptibility to 3' exonucleases is introduction of a free amine to a 3' terminal hydroxyl group of the EGS molecule (see, for example, Orson et al., *Nucl. Acids Res.*, 19: 3435–3441 (1991)). Furthermore, cytosines that may be present in the sequence can be methylated, or an intercalating agent, such as an acridine derivative, can be covalently attached to a 5' terminal phosphate (for example, using a pentamethylene bridge) to reduce the susceptibility of a nucleic acid molecule to intracellular nucleases (see, for example, Maher et al., *Science*, 245: 725–730 (1989); Grigoriev et al., *J. Biol. Chem.*, 267: 3389–3395 (1992)).

Figure 3:
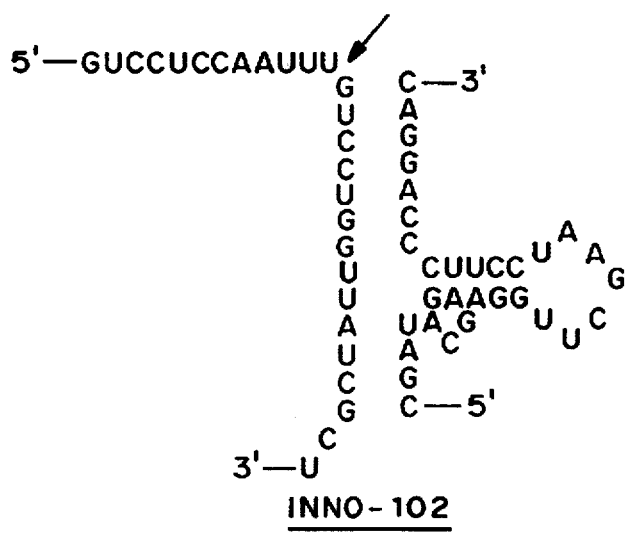
FIG. 3 is a diagram of the structure of EGS with the nucleotide sequence SEQ ID NO. 2 (INNO-102, INNO-102, INNO-102, INNO-102, and INNO-102) or SEQ ID NO. 3 (INNO-139). Nucleotides containing a 2'-O-methyl modification are indicated with underlining.
Figure 3:
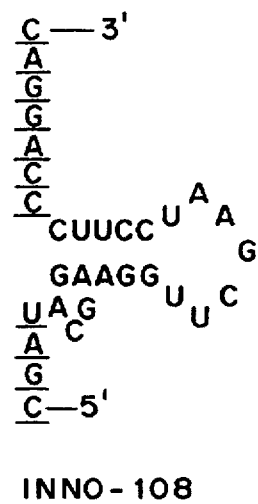
Figure 3:
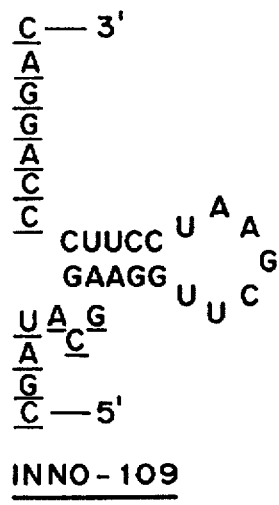
Figure 3:
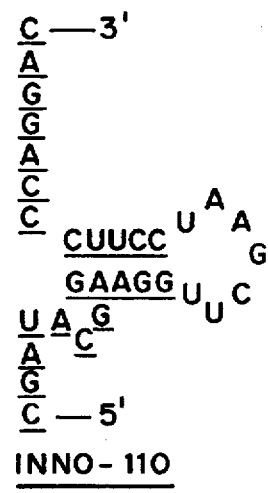
Figure 3:
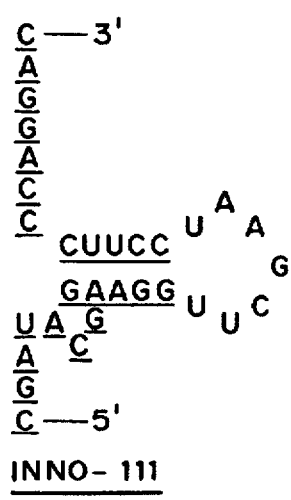
Figure 3:
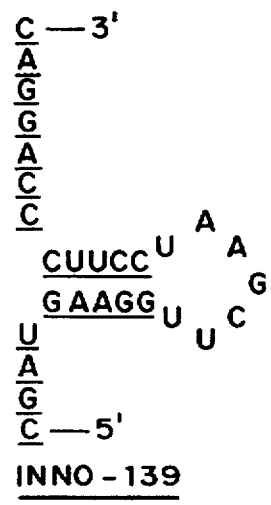

Another class of chemical modifications expected to be useful is modification of the 2' OH group of a nucleotide's ribose moiety, which has been shown to be critical for the activity of the various intracellular and extracellular nucleases. Typical 2' modifications are the synthesis of 2'-O-Methyl oligonucleotides (Paolella et al., *EMBO J.*, 11:1913–1919, 1992) and 2'-fluoro and 2'-amino-oligonucleotides (Pieken, et al., *Science*, 253:314–317, 1991; Heidenreich and Eckstain, *J. Biol. Chem*, 267:1904–1909, 1992). Examples of nuclease-resistant EGS constructs are shown in FIGS. 3 and 6. Portions of EGS molecules can also contain deoxribonucleotides. Such substitutions improve nuclease resistance by eliminating the critical 2' OH group.

B. Chimeric EGS Molecules

The above modifications can be used in limited regions of the EGS molecules and/or in combinations to result in chimeras of modified EGS molecules. Certain regions of EGS molecules are more amenable to modification than others due to the requirement for proper nucleotide interactions to form an active three-dimensional structure. For example, it has been discovered that incorporation of 2'-O-methyl modified nucleotides and phosphorothioate linkages can be introduced into certain regions of an EGS without a significant loss of RNAse P targeting activity. It has also been discovered that 2'-O-methyl ribonucleotides can replace any nucleotides in the sequences complementary to the target sequences and in the T stem. Only a portion of the nucleotides in the T loop can be replaced with 2'-O-methyl nucleotides without significantly affecting ribozyme cleavage. The extent to which such modifications affect the efficiency with which the modified EGS molecule promotes RNAse P-mediated cleavage of hepatitis RNA can readily be determined using the cleavage assay described below. Examples 2 and 3 illustrate possible combinations of modifications and preferred arrangements of modified nucleotides.

III. Cloning and Expression Vectors.

Preferred vectors for introducing EGS molecules into mammalian cells include viral vectors, such as the retroviruses, which introduce DNA which encodes an EGS molecule directly into the nucleus where the DNA is then transcribed to produce the encoded EGS molecule.

Examples of methods for using retroviral vectors for gene therapy are described in U.S. Pat. Nos. 4,868,116 and 4,980,286; PCT applications PCT/US89/03794 and PCT/US89/00422; and Mulligan, *Science*, 260: 926–932 (1993); the teachings of which are incorporated herein by reference.

Defective retroviral vectors, which incorporate their own RNA sequence in the form of DNA into the host chromosome, can be engineered to incorporate an EGS into the cells of a host, where copies of the EGS will be made and released into the cytoplasm or are retained in the nucleus to interact with the target nucleotide sequences of the hepatitis RNA.

Bone marrow stem cells and hematopoietic cells are relatively easily removed and replaced from humans, and provide a self-regenerating population of cells for the propagation of transferred genes. Such cells can be transfected in vitro or in vivo with retrovirus-based vectors encoding EGS molecules. When in vitro transfection of stem cells is performed, once the transfected cells begin producing the particular EGS molecules, the cells can be added back to the patient to establish entire clonal populations of cells that are expressing EGS and are therefore resistant to viral infection, transformation, and other disorders.

As an example, a vector used to clone and express DNA sequences encoding constructs might include:

1. A cloning site in which to insert a DNA sequence encoding an EGS molecule to be expressed.

2. A mammalian origin of replication which allows episomal (non-integrative) replication, such as the origin of replication derived from the Epstein-Barr virus.

3. An origin of replication functional in bacterial cells for producing required quantities of the DNA encoding the EGS constructs, such as the origin of replication derived from the pBR322 plasmid.

4. A promoter, such as one derived from Rous sarcoma virus (RSV), cytomegalovirus (CMV), or the promoter of the mammalian U6 gene (an RNA polymerase III promoter) which directs transcription in mammalian cells of the inserted DNA sequence encoding the EGS construct to be expressed.

5. A mammalian selection marker (optional), such as neomycin or hygromycin resistance, which permits selection of mammalian cells that are transfected with the construct.

6. A bacterial antibiotic resistance marker, such as neomycin or ampicillin resistance, which permits the selection of bacterial cells that are transformed with the plasmid vector.

IV. Therapy

A. Pharmaceutical Compositions

EGS molecules can be used directly in combination with a pharmaceutically acceptable carrier to form a pharmaceutical composition suited for treating a patient. Alternatively, an EGS can be delivered via a vector containing a sequence which encodes and expresses the EGS molecule specific for a particular RNA.

Direct delivery involves the insertion of pre-synthesized EGS molecules into the target cells, usually with the help of lipid complexes (liposomes) to facilitate the crossing of the cell membrane and other molecules, such as antibodies or other small ligands, to maximize targeting. Because of the sensitivity of RNA to degradation, in many instances, directly delivered EGS molecules may be chemically modified, making them nuclease-resistant, as described above. This delivery methodology allows a more precise monitoring of the therapeutic dose.

Vector-mediated delivery involves the infection of the target cells with a self-replicating or a non-replicating system, such as a modified viral vector or a plasmid, which produces a large amount of the EGS encoded in a sequence carried on the vector. Targeting of the cells and the mechanism of entry may be provided by the virus, or, if a plasmid is being used, methods similar to the ones described for direct delivery of EGS molecules can be used. Vector-mediated delivery produces a sustained amount of EGS molecules. It is substantially cheaper and requires less frequent administration than a direct delivery such as intravenous injection of the EGS molecules.

The direct delivery method can be used during the acute critical stages of infection. Preferably, intravenous or subcutaneous injection is used to deliver EGS molecules directly. It is essential that an effective amount of oligonucleotides be delivered in a form which minimizes degradation of the oligonucleotide before it reaches the intended target site.

Most preferably, the pharmaceutical carrier specifically delivers the EGS to affected cells. For example, hepatitis B virus affects liver cells, and therefore, a preferred pharmaceutical carrier delivers anti-hepatitis EGS molecules to liver cells.

B. Delivery of EGS Molecules.

Two methods of delivery may be employed, (1) delivery of synthetic EGS molecules, or (2) delivery of plasmids expressing EGS molecules in a transient fashion. The method of choice will be determined in preclinical studies, using standard methodology, and it is possible that they may be used in combination. Both of them can be efficiently delivered, for example, by using cationic liposome preparations.

A variety of non-vector methods are available for delivering EGS molecules to cells. For example, in general, the EGS molecules, or DNA sequences encoding the EGS molecules, can be incorporated within or on microparticles. As used herein, microparticles include liposomes, virosomes, microspheres and microcapsules formed of synthetic and/or natural polymers. Methods for making microcapsules and microspheres are known to those skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides.

Liposomes can be produced by standard methods such as those reported by Kim, et al., *Biochim. Biophys. Acta*, 728, 339–348 (1983); Liu, D., et al., *Biochim. Biophys. Acta*, 1104, 95–101 (1992); and Lee, et al., *Biochim. Biophys. Acta.*, 1103, 185–197 (1992); Wang, et al., *Biochem.*, 28, 9508–9514 (1989)), incorporated herein by reference. EGS molecules or DNA encoding such molecules, can be encapsulated within liposomes when the molecules are present during the preparation of the microparticles. Briefly, the lipids of choice, dissolved in an organic solvent, are mixed and dried onto the bottom of a glass tube under vacuum. The lipid film is rehydrated using an aqueous buffered solution of the EGS molecules, DNA encoding EGS molecules to be encapsulated, and the resulting hydrated lipid vesicles or liposomes encapsulating the material can then be washed by centrifugation and can be filtered and stored at 4° C. This method has been used to deliver nucleic acid molecules to the nucleus and cytoplasm of cells of the MOLT-3 leukemia cell line (Thierry, A. R. and Dritschilo, A., *Nucl. Acids Res.*, 20: 5691–5698 (1992)). Alternatively, EGS molecules, or DNA encoding such molecules, can be incorporated within microparticles, or bound to the outside of the microparticles, either ionically or covalently.

Cationic liposomes or microcapsules are microparticles that are particularly useful for delivering negatively charged compounds such as nucleic acid-based compounds, which can bind ionically to the positively charged outer surface of these liposomes. Various cationic liposomes have previously been shown to be very effective at delivering nucleic acids or nucleic acid-protein complexes to cells both in vitro and in vivo, as reported by Felgner, P. L. et al., *Proc. Natl. Acad. Sci. USA*, 84: 7413–7417 (1987); Felgner, P. L., *Advanced Drug Delivery Reviews*, 5: 163–187 (1990); Clarenc, J. P. et al., *Anti-Cancer Drug Design*, 8: 81–94 (1993), incorporated herein by reference. Cationic liposomes or microcapsules can be prepared using mixtures including one or more lipids containing a cationic side group in a sufficient quantity such that the liposomes or microcapsules formed from the mixture possess a net positive charge which will ionically bind negatively charged compounds. Examples of positively charged lipids that may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl-]N,N,N-triethylammonium ("DOTMA," see Felgner, P. L. et al., *Proc. Natl. Acad. Sci USA*, 84, 7413–7417 (1987); Felgner, P. L. et al., *Nature*, 337, 387–388 (1989); Felgner, P. L., *Advanced Drug Delivery Reviews*, 5, 163–187 (1990)).

Nucleic acid can also be encapsulated by or coated on cationic liposomes which can be injected intravenously into a mammal. This system has been used to introduce DNA into the cells of multiple tissues of adult mice, including endothelium and bone marrow, where hematopoietic cells reside (see, for example, Zhu et al., *Science*, 261: 209–211 (1993)).

Liposomes containing either EGS molecules or DNA encoding these molecules, can be administered systemically, for example, by intravenous or intraperitoneal administration, in an amount effective for delivery of the anti-hepatitis EGS molecules to targeted cells. Other possible routes include trans-dermal or oral, when used in conjunction with appropriate microparticles. Generally, the total amount of the liposome-associated nucleic acid administered to an individual will be less than the amount of the unassociated nucleic acid that must be administered for the same desired or intended effect.

Compositions including various polymers such as the polylactic acid and polyglycolic acid copolymers, polyethylene, and polyorthoesters and the anti-hepatitis EGS molecules, or DNA encoding such molecules, can be delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., *Drug Delivery Systems* (Chichester, England: Ellis Horwood Ltd., 1987), which can effect a sustained release of the therapeutic anti-hepatitis EGS compositions to the immediate area of the implant.

The following examples are presented for illustrative purposes and additional guidance.

EXAMPLES

Example 1

Oligonucleotide Synthesis and Transcription Reactions for Construction and Analysis of EGS Molecules.
Oligonucleotides:

Oligoribonucleotides (RNA) were prepared according to the method of Ogilvie et al., *Proc. Natl. Acad. Sci. U.S.A.*, 85, 5764–5768 (1988), employing 5'-dimethoxytrityl-2'-methylsilyl-ribonucleoside 3'-CE-phosphoramidites (Biosearch, Massachusetts, or ChemGenes Corp., Massachusetts). 2'-O-methyl oligoribonucleotides (2'-O-methyl RNA) were synthesized using RNA synthesis protocols of, and amidites were purchased from, either Biosearch or Glen Research. Syntheses were performed on a Millipore 8909 Expedite DNA/RNA synthesizer. Controlled pore glass (CPG) were used as the solid support matrix. The coupling time was about 13 min. For the syntheses of analogues containing phosphorothioate linkages, oxidation was replaced by sulfurization which was carried out using Beaucage reagent for 10–15 min. The average coupling yield, as assayed by trityl measurement, was 96–98%.

Cleavage from the support, base and phosphate deprotection, and removal of the 2'-O-TBDMS group were performed as described by Scaringe et al., *Nucleic Acids Research*, 18, 5433–5441 (1990). The crude oligonucleotides in TBAF solution were desalted on a Sephadex G-25 column prior to standard electrophoretic purification using 15–20% polyacrylamide/7M urea gels. Product bands were visualized by UV-shadowing, cut out, and eluted from the gel matrix. The eluted oligomers were finally desalted on a $C_{18}$ Sep-Pak cartridge and quantified by $OD_{260}$ measurement. Homogeneity of the purified analogues was checked by 5'-end labeling or analytical HPLC. They can be further characterized by base composition analysis, as described by Seela, F. and Kaiser, K., *Nucleic Acids Res.*, 15, 3113–3129 (1987), and the content of thioate linkages quantitated by $^{31}$-NMR. Terminal modifications of the 3'-end were made by starting the synthesis from a modified CPG support containing an amino group.

RNAse P Cleavage Assays:

Cleavage reactions were carried out generally according to the procedure described by Yuan, Y., Hwayng, E. S. and Altman, S., *Proc. Natl. Acad. Sci., USA*, 89, 8006–8010, (1992), which is hereby incorporated by reference. Briefly, short substrate reactions were made up to a total volume of 31μ in 50 mM Tris-HCl pH 7.4, 10 mM $MgCl_2$, 25 mM KCl, 0.1 mM EDTA, with an EGS concentration of 200 nM, and a target molecule concentration of 20 nM or less. The amount of RNase P in the assay is saturating. The reactions were incubated at 37° C. for 1 hour. After incubation, the reaction solution was mixed with loading buffer (98% formamide, 10 mM EDTA, 0.025% bromophenol blue). The cleaved substrate was separated from the uncleaved by electrophoresis on a 15% acrylamide gel containing 7M urea. The bands were quantified on a Molecular Dynamics Phophorimager.

The bands corresponding to the precursor RNA substrate and the resulting two cleavage products were counted from the dried gel using a Betascope gel analyzer (Betagen).

RNAse P was purified by DEAE Sepharose chromatography and glycerol density gradient centrifugation essentially as described by Bartkiewicz et al., *Genes Dev.* 3, 488–499 (1989), which is hereby incorporated by reference.

To test cleavage with a longer target RNA molecules, different reaction conditions were used. Reactions in a total volume of 10 μl contained 40 mM Tris-HCl (pH 7.4), 10 mM $MgCl_2$, 1 mM spermidine 10 mM dithiothreitol, 0.05 μg/μl nuclease-free bovine serum albumin, 0.01% (v/v) Triton-X100, 0.8 Units/μl RNASIN, 0.2 mM ATP, 0.2 mM GTP, 0.2 mM UTP, 0.2 mM CTP, 0.1 μCi/μl [$a^{32}P$] CTP, 2 mM $m^7G(5')pppG$, 0.06 μg/μl yeast RNA, 25 mM KCl, 3 Units T7 RNA polymerase, 250 nM EGS, 1 μl of human RNAse P and 3 ng/μl linearized plasmid. Reactions were initiated by the addition of linearized plasmid and incubated for 30 minutes at 37° C. Reactions were terminated by the addition of 10 μl of 80% formamide, 10 mM EDTA, 0.1% bromphenol blue. After heating for 2 min at 90° C., samples were electrophoresed for 2 hours at 48 watts on a 5% denaturing polyacrylamide gel. After vacuum drying for 1 hour at 60° C., the gel was analyzed by phosphoimaging.

The percentage of precursor RNA substrate remaining in either assay was plotted as function of the EGS concentration and the catalytic efficiency expressed as $k_{cat}/K_m$ (where $k_{cat}$ is the rate constant of cleavage and $K_m$ is the Michaelis constant), the second order rate constant for the reaction of free EGS and substrate. Following the methods of Heidenreich and Eckstein (*J. Biol. Chem.*, 267: 1904–1909 (1992), the efficiency of the cleavage reaction, $k_{cat}/K_m$), was determined using the formula $$-\ln F/t = (k_{cat}/K_m)[C]$$

where F is the fraction of RNA substrate left, t is the reaction time, and [C] is the EGS concentration.

Fetal Calf Serum Stability Assay:

The nuclease resistance of modified EGS molecules were tested in a Fetal Calf Serum (FCS) Assay. It was reported by Shaw et al., *Nucleic Acids Res.* 19, 747–750 (1991), that 10% FCS, when heated inactivated, mimics rather closely the human serum. The assay conditions were very similar to that previously described by Hoke et al., *Nucleic Acids Res.* 19, 5743–5748 (1991). Briefly, an EGS analog to be tested was 5'-end labeled with T4 polynucleotide kinase and [$\gamma$-$^{35}S$] ATP (this procedure can generate radiolabeled oligonucleotides which are resistant against dephosphorylation). The labeled EGS was then purified by phenol/chloroform extraction, followed by a Sephadex G-25 spin-column filtration. The purified EGS was mixed with cold EGS and 10% heat-inactivated fetal calf serum (FCS) so that the final concentration of EGS was about 5 μM. EGS analogues were treated over a period of 24 hours. Aliquots were withdrawn from the reaction mixture at different time points, mixed with 2× loading dye, heat inactivated at 90° C. for 3 min, then stored at −20° C. The results were analyzed on 12% polyacrylamide/7M urea gels.

Example 2

Construction EGS molecules mediating RNAse P cleavage of HBsAg RNA

Human external guide sequence (EGS) molecules were designed to yield cleavage by RNAse P in RNA encoding HBsAg. In the presence of target, the EGS molecules formed a tRNA-like structure which elicited cleavage by RNAse P.

EGS Constructs Targeted to HBsAg:

EGS sequences HBV102 (SEQ ID NO. 2), HBV#1 (SEQ ID NO. 5) and HBV#2 (SEQ ID NO. 6) were designed to target conserved regions of RNA encoding hepatitis B surface antigen (HBsAg). As shown in FIG. 2, the sequence of one of the recognition arms (the A recognition arm; nt 25 to 31 of SEQ ID NO. 2) of HBV102 is complementary to seven nucleotides in the sequence encoding HBsAg (nt 13 to 19 of SEQ ID No. 1). The sequence of the other recognition arm (the D recognition arm; nt 1 to 4 of SEQ ID NO. 2) of HBV102 is complementary to four nucleotides in the sequence encoding HBsAg (nt 22 to 25 of SEQ ID No. 1). Thus, the target sequence contains two regions complementary to the two recognition arms of the EGS which are separated by two unpaired nucleotides.

EGS without a variable loop:

EGS construct HBV140 (SEQ ID NO. 3) was designed to target the same conserved region of RNA encoding hepatitis B surface antigen as HBV102. The recognition arms of HBV140 have the same sequence as the recognition arms of HBV102. Specifically, the sequence of the A recognition arms (nt 22 to 28 of SEQ ID NO. 3) of HBV140 is complementary to seven nucleotides in the sequence encoding HBsAg (nt 13 to 19 of SEQ ID No. 1). The sequence of the D recognition arm (nt 1 to 4 of SEQ ID NO. 3) of HBV140 is complementary to four nucleotides in the sequence encoding HBsAg (nt 22 to 25 of SEQ ID No. 1). EGS HBV140 is only 28 nucleotides long.

2'-O-methyl-containing EGS molecules:

Several EGS molecules based on HBV102 and HBV140 were prepared containing some 2'-O-methyl nucleotides. These oligonucleotides were prepared in an automated oligonucleotide synthesizer as described earlier except that the nucleotide reagents contained a 2'-O-methyl group. The average coupling yield, as assayed by trityl measurements, was in the range of 96 to 98%. Upon completion of deprotection, fully deprotected oligonucleotides were purified by denaturing gel electrophoresis and their purity assessed by 5'-end labeling, analytical HPLC, base composition analysis and $^{31}$P-NMR. FIG. 3 shows some of the modified EGS molecules that were constructed. This series allowed testing of the extent to which an EGS molecule could be 2'-O-methylated and still retain EGS function and the extent of nuclease resistance conferred by these modifications.

2'-O-methyl/Phosphorothioate chimeric EGS molecules:

Several EGS molecules based on HBV102 and HBV140 were prepared containing phosphorothioate nucleotide linkages as well as some 2'-O-methyl nucleotides. Different regions of the EGS molecules were unmodified, 2'-O-methylated, thiolated, or both. The resulting molecules are modification chimeras. These oligonucleotides were prepared in an automated oligonucleotide synthesizer as described earlier except that the nucleotide reagents contained a 2'-O-methyl group as described above. Sulfurization was performed using Beaucage reagent for 10 to 15 minutes. FIG. 3 shows some of the modified EGS molecules that were constructed. This series allowed testing of the extent to which an EGS molecule could be 2'-O-methylated and still retain EGS function and the extent of nuclease resistance conferred by these modifications.

Example 3

Measuring EGS Cleavage Activity.

The EGS constructs described in Example 2 were assayed using the RNAse P cleavage assays described in Example 1 to determine the efficiency of the cleavage reaction. FIG. 1 depicts the model system using a short substrate which was used to evaluate the ability of modified EGS molecules in inducing RNase P-mediated target cleavage. The sequence of the short substrate (SEQ ID NO. 1) was derived from the full-length pre-genomic HBV RNA. The data is presented in FIGS. 4, 5 and 6.

2'-O-methyl Substitutions.

Figure 4:
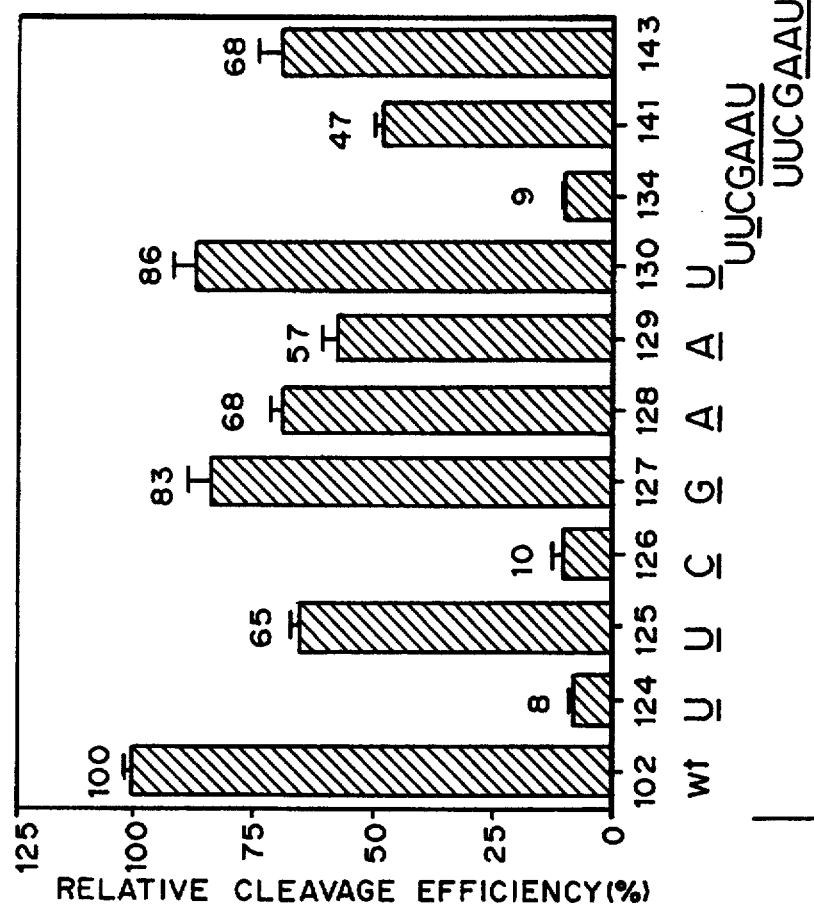
FIG. 4 is a graph of the cleavage efficiency of the EGS molecules shown in FIG. 3.

2'-O-methyl-oligoribonucleotides have several favorable features as a logical choice to modify. The synthesis of these analogues is very similar to that of the DNA synthesis; they have a much better binding affinity to RNA target than DNA analogues and the resulting duplexes have a structure between that of a RNA-RNA duplex (A-form) and DNA-DNA duplex (B-form). In addition, they prove to be fairly resistant to degradation by either RNA- or DNA-specific nucleases. FIG. 3 illustrates a serial sequential substitutions of different segments of an all-RNA EGS (INNO-102) with 2'-O-methyl residues. Substituted nucleotides are indicated by underlining. As indicated in FIG. 4, substitutions of the recognition sequences (INNO-108) did not affect the efficiency of RNase P-mediated target cleavage relative to the wild-type EGS. On the other hand, further replacements of the variable loop (INNO-109) and T stem (INNO-110) did lead to a progressive and additive decrease in activity. However, much of the lost activity can be restored by deleting the variable loop (INNO-139). As a result, substitutions of the recognition sequences and the T stem of the all-RNA EGS by 2'-O-methyl RNA residues were well tolerated by RNase P. In sharp contrast, replacement of the 7 nucleotides in the T loop (INNO-111) resulted in modified EGS with virtually no activity. This result indicates that several or all of the RNA residues in the T loop are critical for maintaining either the correct tertiary structure(s) of EGS and/or specific interactions with RNase P.

T loop Modifications.

Figure 5:
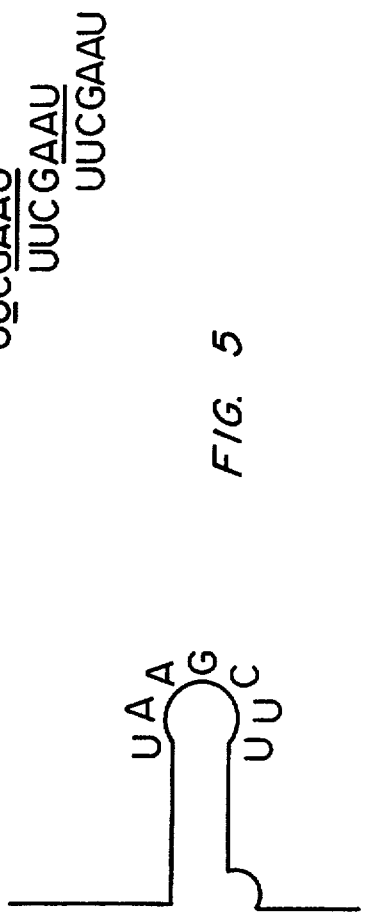
FIG. 5 is a graph of the relative RNAse P cleavage efficiency (%) of various EGS molecules having the nucleotide sequence SEQ ID NO. 2. All of the EGS molecules assayed, except INNO-102 (wt), were completely 2-O-methyl modified in both recognition arms, the variable loop and the T stem. Additional modifications to each EGS are indicated underneath the corresponding graph bar. 2'-O-methyl modifications are indicated with underlining. Nucleotides with 5'-phosphorothioate groups are indicated with outline text.

The purpose of this series of modifications was to identify the residue(s) responsible for the loss of EGS activity and subsequently to develop alternative strategies for the generation of nuclease resistant EGS analogues. To this end, seven analogues were designed and tested. Each of these analogues had a completely 2'-O-methyl substituted recognition sequence, variable loop and T stem. In addition, one of the seven residues in the T loop was also replaced with a 2'-O-methyl group while the remaining six positions were kept as intact RNA (FIG. 5). The results of cleavage assay showed that the first 5'-U (INNO-124) and the third 5'-C (INNO-126) caused the most pronounced decrease in cleavage efficiency. Analogue 134 where all residues were substituted with 2'-O-methyl RNA except these two critical residues was subsequently tested. Unfortunately, analogue 134 still had very little activity. This could imply that the T loop must adopt a rather coordinate structure, and accumulation of the 2'-O-methyl residues in this region seems to disturb significantly such a structure. Non-negligible loss of activity was also accounted with analogue 141 in which three of the seven residues in the T loop were replaced by 2'-O-methyl residues. On the basis of these data, another type of modifications was employed, replacing the phosphodiester backbone with phosphorothioate backbone. The combination of these two types of modifications generated a fully modified analogue 143 in which the T loop region was substituted by phosphorothioate RNA and the rest of the molecule by 2'-O methyl residues. As assayed by cleavage assay, this chimeric EGS analogue still retained about 70% of that of the wild-type activity.

Backbone Modifications.

While 2'-O-methyl substitutions can confer significant nuclease resistance to unmodified EGS, further enhancement of the stability by the introduction of modified backbones was investigated. For example, a series of 2'-O-methyl phosphorothioate substitutions was examined. Starting from the fully modified EGS 143, phosphorothioate linkages were selectively added to different regions of this molecule (FIG. 6, INNO-151 to INNO-154). However, in vitro cleavage analysis of these analogues indicated that substitutions with these doubly-modified residues were causing a rather significant and additive loss of activity. Since several studies have shown that simple modifications at the ends of an oligonucleotide can provide additional nuclease resistance, analogue 155 in which the four terminal phosphodiester linkages (two from the 3'-end and two from the 5'-end) were replaced with phosphorothioate backbones was synthesized and tested. As shown in FIG. 6, the end-capped EGS analogue 155 was still capable of inducing an efficient target cleavage when assayed with a purified preparation of human RNase P.

Terminal Modifications.

Figure 8:
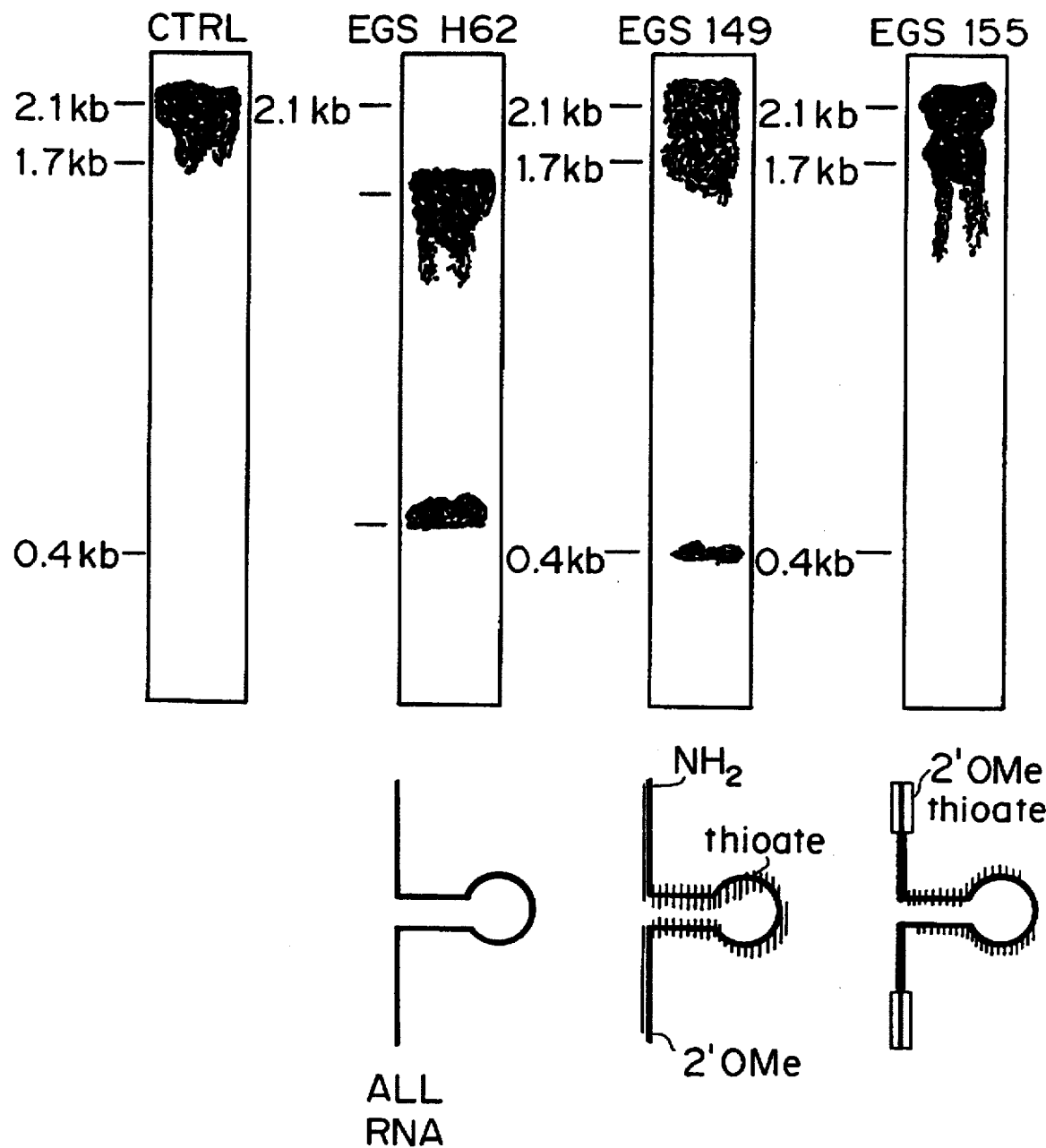
FIG. 8 is a diagram showing RNAse P-mediated cleavage assays of 2.1 kb HBV transcript by all-RNA and chemically modified EGS molecules. Modifications to each EGS are indicated diagrammatically underneath the corresponding gel lane.
Figure 9:
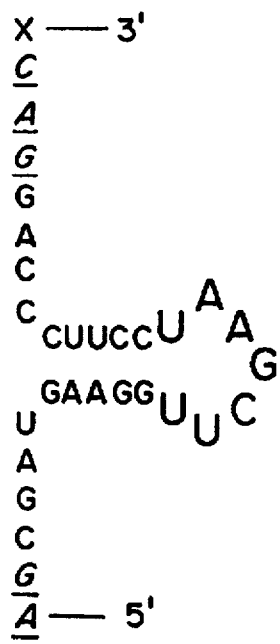
FIG. 9 is a diagram of the structure of an EGS with the nucleotide sequence SEQ ID NO. 5 and with chemical modifications in specific regions.
Figure 10:
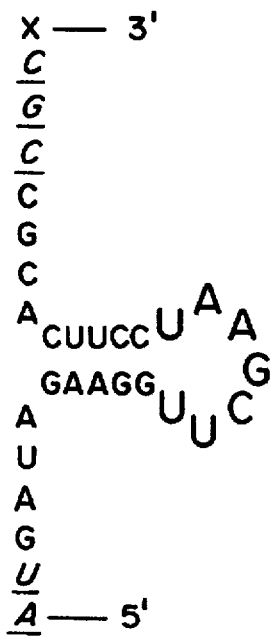
FIG. 10 is a diagram of the structure of an EGS with the nucleotide sequence SEQ ID NO. 6 and with chemical modifications in specific regions.
Figure 11:
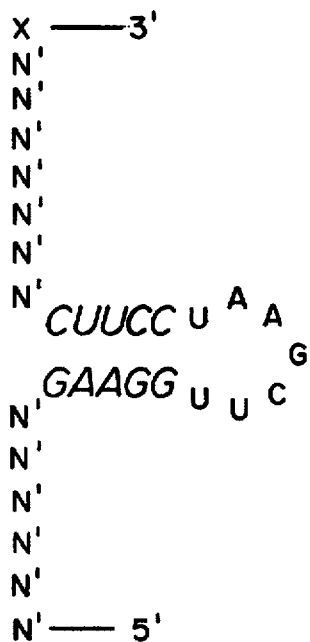
FIG. 11 is a diagram of the structure of an EGS with the nucleotide sequence SEQ ID NO. 4 and with chemical modifications in specific regions.
Figure 12:
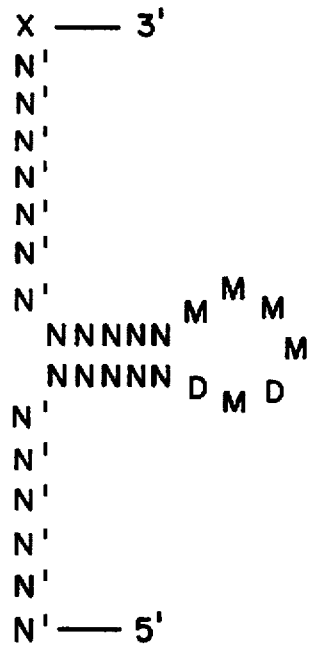
FIG. 12 is a diagram of the structure of an EGS with the nucleotide sequence SEQ ID NO. 7 and with chemical modifications in specific regions.

Two types of terminal modifications were assayed. In one case, both 3' and 5' ends were capped with two 2'-O-methyl phosphorothioate linkages (INNO-155); in another case, the 3'-end was protected with amino group by starting the synthesis from a modified CPG support (INNO-149). As illustrated in FIG. 8, both analogues were capable of inducing RNase P-mediated cleavage of a 2.1 kb HBV RNA although analogue 149 seems to be more effective than analogue 155.

Cleavage of Large Target RNA.

Plasmid pAYW2.1, containing the sequence that encodes the 2.1 kb RNA of the AYW strain of HBV, was linearized by digestion with Not I, and then transcribed by T7 RNA polymerase in the presence of [$\alpha^{32}$P]CTP. Labeled transcripts were incubated for 30 min at 37° C. with RNase P in the presence of various EGS molecules. Reaction products were subjected to denaturing polyacrylamide gel electrophoresis, and analyzed by phosphoimaging. EGS-mediated cleavage at the targeted site of the 2.1 kb transcript produces cleavage products that are approximately 1.7 and 4 kb in length. The results are shown in FIG. 8.

For lane 1 (CTRL), transcripts were incubated with CAT-9 EGS, described in Yuan, Y. and Altman, S., *Science*, 263, 1269–1273 (1994). CAT-9 EGS has no activity against HBV transcripts. As expected, no cleavage was detected. For lane 2 (EGS H62), transcripts were incubated with EGS H62, an all-RNA EGS, having the sequence of SEQ ID NO. 3, that was prepared by T7 RNA polymerase transcription of a DNA oligonucleotide. Complete cleavage of the 2.1 kb RNA was observed. For lane 3 (EGS 149), transcripts were incubated with INNO-149, a chemically synthesized RNA, having the sequence of SEQ ID NO. 3, that was modified by (1) 2'-O-methyl in each position of the A recognition arm, T stem and D recognition arm, (2) phosphorothioate in each position of the T loop, and (3) a 3'-amino group. The 2.1 kb RNA was observed to be mostly cleaved by this EGS. For lane 4 (EGS 155), transcripts were incubated with INNO-155, a chemically synthesized RNA, having the sequence of SEQ ID NO. 3, that was modified by (1) 2'-O-methyl in last 4 positions of the A recognition arm, in the first 4 positions of the D recognition arm, and in each position of the T stem, (2) phosphorothioate in each position of the T loop, and (3) 2'-O-methyl phosphorothioate in the first 3 positions of the A recognition arm and in the last 3 positions of the D recognition arm. The 2.1 kb was observed to be partially cleaved by this EGS.

Figure 13:
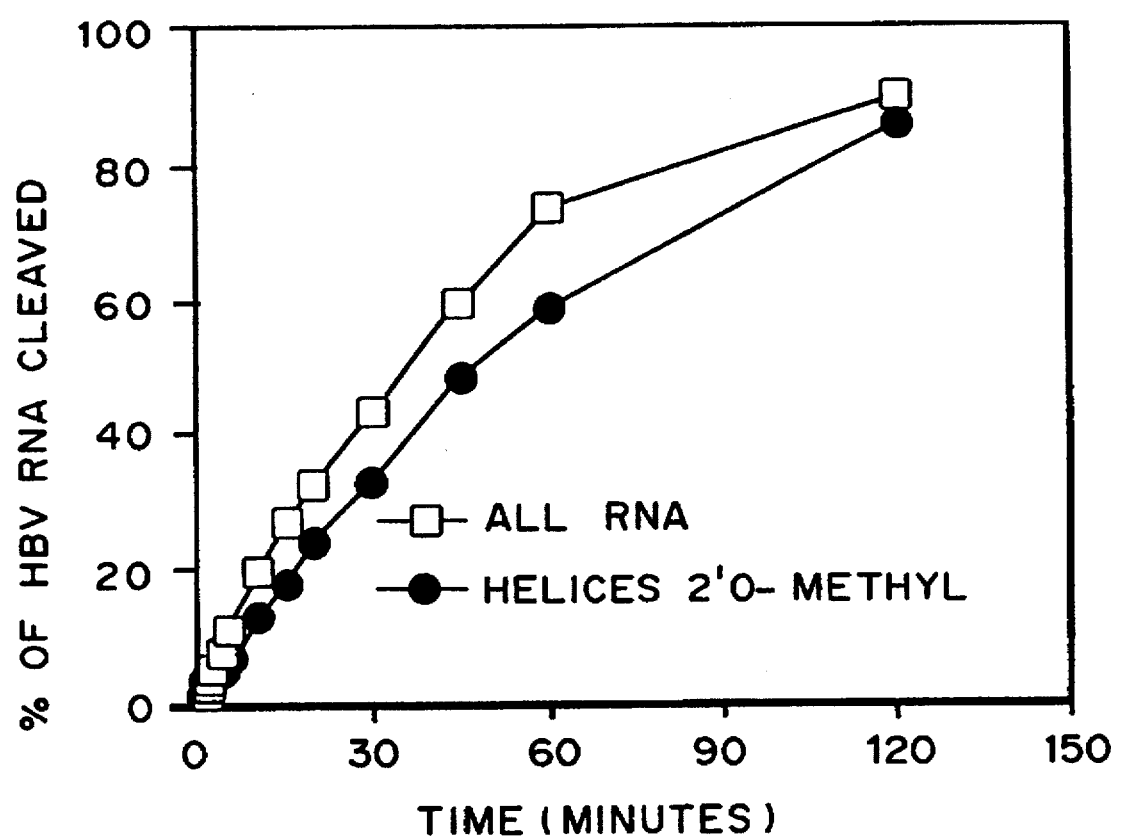
FIG. 13 is a graph showing turnover of EGS molecules in cleavage assays. The graph plots percent of HBV substrate cleaved versus time of incubation.

Turnover of EGS-mediated cleavage was measured using the short substrate assay described in Example 1 with INNO-140 and INNO-139 (shown in FIG. 3), each at a concentration of 20 nM. The target molecule was at a concentration of 400 nM, which is a 20 fold excess. At various time points, 2 µl aliquots were removed and the reaction quenched in 10 µl loading buffer. The results are shown in FIG. 13. Clearly 2'-O-methyl modification to the recognition arms and t loop do not significantly affects turnover.

Example 4

Measuring EGS Stability.

In order to evaluate the effect of different modifications on increasing the nuclease resistance of modified EGS molecules, the EGS constructs described in Example 2 were assayed using the Fetal Calf Serum assay described in Example 1. The results are summarized in FIG. 7. As expected, the all-RNA EGS (INNO-140) had a very short half-life in 10% FCS (less than 10 min). The half-life of the 2'-O-methyl substituted INNO-139 was greatly increased but still relatively short, probably due to the presence of an unmodified all-RNA T loop. Replacement of the T loop with phosphorothioate RNA (INNO-143) increased the half-life from 2 hours to approximately 10 hours, and additions of the two 2'-O-methyl phosphorothioate caps (INNO-155) further increased the half-life to more than 18 hours.

Modifications and variations of the method of the present invention will be obvious to those skilled in the art from the foregoing detailed description. Such modifications and variations are intended to come within the scope of the appended claims.

We claim:

1. An external guide sequence comprising an isolated oligonucleotide molecule comprising a RNAse P cleavage targeting sequence, and a recognition sequence complementary to a targeted sequence in a target RNA molecule, wherein the external guide sequence promotes RNAse P-mediated cleavage of the target RNA molecule, and wherein at least one nucleotide in the external guide sequence is selected from the group consisting of modified nucleotides and unmodified deoxyribonucleotides.

2. The external guide sequence of claim 1 wherein the target RNA molecule is a hepatitis B RNA molecule.

3. The external guide sequence of claim 1 comprising a RNAse P cleavage targeting sequence, a recognition sequence complementary to a targeted sequence in the target RNA molecule, and a RNA sequence binding to a ligand, wherein at least one nucleotide in the external guide sequence is selected from the group consisting of modified nucleotides and unmodified deoxyribonucleotides, and wherein the external guide sequence promotes cleavage of the target RNA molecule by RNAse P only when bound to the ligand.

4. The external guide sequence of claim 1 comprising a RNAse P cleavage targeting sequence, a recognition sequence complementary to a targeted sequence in the target RNA molecule, and a RNA sequence binding to a ligand, wherein at least one nucleotide in the external guide sequence is selected from the group consisting of modified nucleotides and unmodified deoxyribonucleotides, and wherein the external guide sequence promotes cleavage of the target RNA molecule by RNAse P only when not bound to the ligand.

5. A composition for promoting cleavage of a target RNA molecule wherein the composition comprises the external guide sequence of claim 1 in a pharmaceutically acceptable delivery system.

6. The composition of claim 5 wherein the pharmaceutically acceptable delivery system is selected from the group consisting of liposomes, virosomes, microspheres and microcapsules.

7. The external guide sequence of claim 1 wherein one or more of the 2' hydroxyl groups of ribonucleotides are replaced with a chemical group selected from the group consisting of hydrogen, an O-alkyl group, an amino group, and fluorine, wherein one or more of the phosphate linking groups are replaced with a linking group selected from the group consisting of methyl phosphonate and phosphorothioate, and wherein the modification increases resistance of the external guide sequence to nucleases.

8. The external guide sequence of claim 7 wherein one or more of the 2' hydroxyl groups of the ribonucleotides are replaced with hydrogen or a methoxy group; and wherein one or more of the phosphate linking groups are replaced with phosphorothioate.

9. The external guide sequence of claim 1 wherein the recognition sequence comprises an A recognition arm and a D recognition arm, wherein the A recognition arm is located at the 3' end of the external guide sequence and the D recognition arm is located at the 5'0 end of the external guide sequence.

10. The external guide sequence of claim 9 having the structure $$\begin{array}{c} 3' \\ R \\ Y_n \\ Y \\ Y \\ Y \\ Y \\ Y \\ Y \quad {}_L{}^L \\ JJJJ \quad \quad L \\ JJJJ \quad {}_{S_L}S \\ Y_m \\ 5' \end{array}$$

where

R represents 3'-OH, 3'-OPO(O)OCH$_2$CH(OH)-CH$_2$NH$_2$, or 3'-OPO(S)OCH$_2$CH(OH)CH$_2$NH$_2$ Y represents a 2'-O-methyl ribonucleotide with either a 5'-phosphate or a 5'-phosphorothioate, J represents a 2'-O-methyl ribonucleotide with a 5'-phosphate, L represents either a 2'-O-methyl ribonucleotide with a 5'-phosphate, or a ribonucleotide with 5'-phosphorothioate, S represents a ribonucleotide with 5'-phosphorothioate, and where n is greater than 0, m is greater than 0, and the total of n and m is greater than 3.

11. The external guide sequence of claim 9 having the structure $$\begin{array}{c} 3' \\ R \\ Y_n \\ Y \\ Y \\ Y \\ Y \\ Y \\ Y \quad {}_u{}^A \\ CUUCC \quad \quad A \\ GAAGG \quad \quad G \\ Y_m \quad {}_U{}^C \\ 5' \end{array}$$

where

R represents 3'-OH, 3'-OPO(O)OCH$_2$CH(OH)-CH$_2$NH$_2$, or 3'-OPO(S)OCH$_2$CH(OH)CH$_2$NH$_2$ Y represents a 2'-O-methyl ribonucleotide with either a 5'-phosphate or a 5'-phosphorothioate, A, C, G, and U represent the indicated 2'-O-methyl ribonucleotide with a 5'-phosphate, A, C, G, and U represent the indicated ribonucleotide with a 5'-phosphorothioate, and where n is greater than 0, m is greater than 0, and the total of n and m is greater than 3.

12. The external guide sequence of claim 9 having the structure

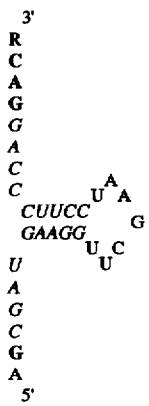

where

R represents 3'-OH, 3'-OPO(O)OCH$_2$CH(OH)-CH$_2$NH$_2$, or 3'-OPO(S)OCH$_2$CH(OH)CH$_2$NH$_2$ A, C, G, and U represent the indicated 2'-O-methyl ribonucleotide with a 5'-phosphate, A, C, G, and U represent the indicated 2'-O-methyl ribonucleotide with a 5'-phosphorothioate, A, C, G, and U represent the indicated ribonucleotide with a 5'-phosphorothioate.

13. The external guide sequence of claim 9 having the structure

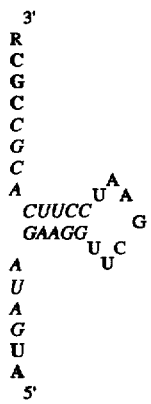

where

R represents 3'-OH, 3'-OPO(O)OCH$_2$CH(OH)-CH$_2$NH$_2$, or 3'-OPO(S)OCH$_2$CH(OH)CH$_2$NH$_2$ A, C, G, and U represent the indicated 2'-O-methyl ribonucleotide with a 5'-phosphate, A, C, G, and U represent the indicated 2'-O-methyl ribonucleotide with a 5'-phosphorothioate, A, C, G, and U represent the indicated ribonucleotide with a 5'-phosphorothioate.

14. The external guide sequence of claim 9 comprising the structure

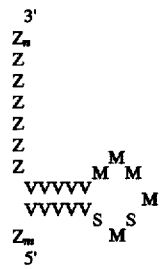

where

Z represents a nucleotide having (a) a chemical group attached to the 2' carbon selected from the group consisting of hydroxyl, hydrogen, O-alkyl, amino, and fluorine, and (b) a 5' linking group selected from the group consisting of phosphate, methyl phosphonate, and phosphorothioate, V represents a nucleotide having a chemical group attached to the 2' carbon selected from the group consisting of hydroxyl, hydrogen, O-alkyl, amino, and fluorine, M represents a nucleotide having either (a) a 5' phosphate and a chemical group attached to the 2' carbon selected from the group consisting of hydroxyl, hydrogen, O-alkyl, amino, and fluorine, or (b) a hydroxyl attached to the 2' carbon and a 5' linking group selected from the group consisting of phosphate, methyl phosphonate, and phosphorothioate, S represents a nucleotide having a 5' linking group selected from the group consisting of phosphate, methyl phosphonate, and phosphorothioate, and where n is greater than 0, m is greater than 0, and the total of n and m is greater than 3.

15. The external guide sequence of claim 9 having the structure

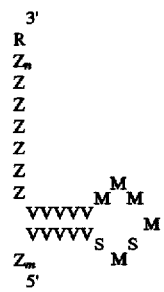

where

R represents 3'-OH, 3'-OPO(O)OCH$_2$CH(OH)-CH$_2$NH$_2$, or 3'-OPO(S)OCH$_2$CH(OH)CH$_2$NH$_2$ Z represents a 2'-O-methyl ribonucleotide with a 5'-phosphate, a 2'-O-methyl ribonucleotide with a 5'-phosphorothioate, a ribonucleotide with 5'-phosphate, or a ribonucleotide with 5'-phosphorothioate, V represents a 2'-O-methyl ribonucleotide with a 5'-phosphate or a ribonucleotide with 5'-phosphate, M represents either a 2'-O-methyl ribonucleotide with a 5'-phosphate, or a ribonucleotide with 5'-phosphorothioate, S represents a ribonucleotide with 5'-phosphate or a ribonucleotide with 5' phosphorothioate, and where n is greater than 0, m is greater than 0, and the total of n and m is greater than 3.

16. The external guide sequence of claim 15 wherein the target RNA molecule is a hepatitis B RNA molecule.

17. An external guide sequence comprising a nucleotide base sequence selected from the group consisting of SEQ ID NO. 2, SEQ ID NO. 3, SEQ ID NO. 5, and SEQ ID NO. 6.

18. An external guide sequence comprising an isolated oligonucleotide molecule comprising a RNAse P cleavage targeting sequence, and a recognition sequence complementary to a targeted sequence in a hepatitis B RNA molecule, wherein the external guide sequence promotes RNAse P-mediated cleavage of the hepatitis B RNA molecule.

19. A method for cleaving a target RNA molecule comprising bringing into contact, under conditions that promote RNAse P cleavage, RNAse P, the target RNA molecule, and an external guide sequence which comprises an isolated oligonucleotide molecule comprising a RNAse P cleavage targeting sequence, and a recognition sequence complementary to a targeted sequence in a target RNA molecule, wherein the external guide sequence promotes RNAse P-mediated cleavage of the target RNA molecule, and wherein at least one nucleotide in the external guide sequence is selected from the group consisting of modified nucleotides and unmodified deoxyribonucleotides.

20. The method of claim 19 wherein the target RNA molecule is a hepatitis B RNA molecule, wherein the step of bringing into contact is accomplished by administering to cells the external guide sequence, and wherein the external guide sequence is in a pharmaceutically acceptable delivery system.

21. The method of claim 20 wherein the pharmaceutically acceptable delivery system is selected from the group consisting of liposomes, virosomes, microspheres and microcapsules.

22. An engineered expression vector encoding an external guide sequence comprising an isolated oligonucleotide molecule comprising a RNAse P cleavage targeting sequence, and a recognition sequence complementary to a targeted sequence in a hepatitis B RNA molecule, wherein the external guide sequence promotes RNAse P-mediated cleavage of the hepatitis B RNA molecule.

23. A composition for promoting cleavage of a hepatitis B RNA molecule wherein the composition comprises the engineered expression vector of claim 22 in a pharmaceutically acceptable delivery system.

24. The composition of claim 23 wherein the pharmaceutically acceptable delivery system is selected from the group consisting of liposomes, virosomes, microspheres and microcapsules.

25. A method of inhibiting hepatitis B virus comprising administering to cells an engineered expression vector encoding an external guide sequence comprising a RNAse P cleavage targeting sequence, and a recognition sequence complementary to a targeted sequence in a hepatitis B RNA molecule, wherein the external guide sequence promotes RNAse P-mediated cleavage of the hepatitis B RNA molecule.

26. The method of claim 25 wherein the vector is a viral vector selected from the group consisting of retroviral vectors, adeno-associated viral vectors and Epstein-Barr viral vectors.

27. The method of claim 25 wherein the engineered expression vector is in a pharmaceutically acceptable delivery system.

28. The composition of claim 27 wherein the pharmaceutically acceptable delivery system is selected from the group consisting of liposomes, virosomes, microspheres and microcapsules.

29. The method of claim 28 wherein the pharmaceutically acceptable delivery system is a liposome.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:1:

GUCCUCCAAU UUGUCCUGGU UAUCGCUGGA UGUUGUC 37

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:2:

CGAUACGGAA GGUUCGAAUC CUUCCCAGGA C 31

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:3:

CGAUGAAGGU UCGAAUCCUU CCCAGGAC 28

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:4:

NNNNNGAAG GUUCGAAUCC UUCNNNNNNN 30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:5:

AGCGAUGAAG GUUCGAAUCC UUCCCAGGAC                    30

( 2 ) INFORMATION FOR SEQ ID NO:6:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:6:

AUGAUAGAAG GUUCGAAUCC UUCACGCCGC                    30

( 2 ) INFORMATION FOR SEQ ID NO:7:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:7:

NNNNNNNNN NNNNNNNNN NNNNNNNNN                       30

( 2 ) INFORMATION FOR SEQ ID NO:8:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:8:

NNNNNNNNNN NNNNNNNNNN NNNNNNNNN                     29

( 2 ) INFORMATION FOR SEQ ID NO:9:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:9:

NNNNGAAGGU UCGAAUCCUU CNNNNNNNNN N                  31